US00PP36857P2

(12) United States Plant Patent
Villegas

(10) Patent No.: US PP36,857 P2
(45) Date of Patent: Jul. 22, 2025

(54) ***SANSEVIERIA* PLANT NAMED 'WHITE STAR'**

(50) Latin Name: *Sansevieria aubrytiana*
Varietal Denomination: WHITE STAR

(71) Applicant: FLORICA FARMS, INC., Orlando, FL (US)

(72) Inventor: Marvin Gonzalez Villegas, Alajuela (CR)

(73) Assignee: Florica Farms, Inc., Orlando, FL (US)

( * ) Notice: Subject to any disclaimer, the term of this patent is extended or adjusted under 35 U.S.C. 154(b) by 0 days.

(21) Appl. No.: 18/765,186

(22) Filed: Jul. 5, 2024

(51) Int. Cl.
*A01H 5/12* (2018.01)
*A01H 6/12* (2018.01)

(52) U.S. Cl.
USPC ..... Plt./382

(58) Field of Classification Search
USPC ..... Plt./382
CPC ..... A01H 5/12; A01H 5/00; A01H 6/12
See application file for complete search history.

(56) References Cited

U.S. PATENT DOCUMENTS

PP34,061 P2 * 3/2022 Villegas ..... Plt./382

* cited by examiner

*Primary Examiner* — June Hwu
(74) *Attorney, Agent, or Firm* — Foley & Lardner LLP

(57) ABSTRACT

A new and distinct cultivar of *Sansevieria aubrytiana* plant named 'WHITE STAR' particularly characterized by its variegated foliage with dark and light green, and white colored irregular bands in the front and backside of the leaf blade. supported in a rosette; 55-75 cm plant height; erect plant habit, moderate drought tolerance with low need for water and resistant to anthracnose (*Colletotrichum sansevieriae*) disease.

3 Drawing Sheets

Figure 1:
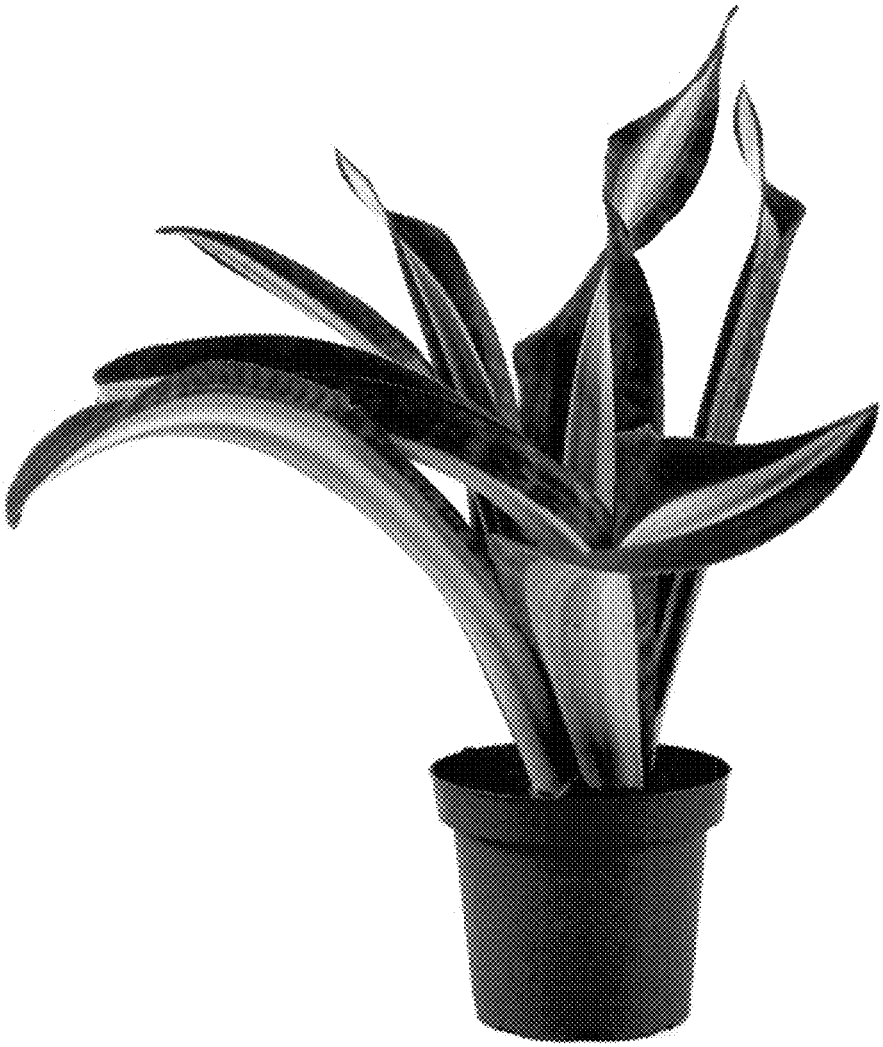

Latin name of the genus and species of the claimed plant: *Sansevieria aubrytiana.*

VARIETY DENOMINATION

BACKGROUND OF THE INVENTION

The present invention relates to a new and distinct cultivar of *Sansevieria* plant, botanically known as *Sansevieria aubrytiana*, of the family Asparagaceae, hereinafter referred to by the cultivar name 'WHITE STAR'.

*Sansevieria* is a monocotyledonous flowering plant which can be grown from either hard-leafed or soft-leafed varieties for interior use as a house plant or outdoors ornamental plant.

The new *Sansevieria* 'WHITE STAR', originated from a naturally occurring mutation of the *Sansevieria* 'Marlowe' (U.S. Plant Pat. No. 34,061). The new *Sansevieria* 'WHITE STAR' was discovered and selected in a ground outfield area by the inventor, Marvin Gonzalez Villegas, as a single sprouting rare, mutation in a 'Marlowe' plantation in a controlled environment in Monterrey, San Carlos, Alajuela Province, Costa Rica.

Asexual reproduction of the new *Sansevieria* cultivar by vegetative cuttings was first performed in July 2022 in Monterrey, San Carlos, Alajuela Province, Costa Rica, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'WHITE STAR', which in combination distinguish this *Sansevieria* as a new and distinct cultivar:

1. Variegated foliage with different green and white tones on the irregular bands in the front and backside of the leaf blade.
2. Wide and curved lanceolate leaves, 55-75 cm long and supported in a rosette disposition.
3. 55-75 cm plant height.
4. Plant habit: Erect.
5. Needs little water and is moderately drought tolerant.

The new variety 'WHITE STAR' presents an average of 5-7 leaves per plant when it reaches its maturity (between 6-9 months). The new variety has an erect growth habit, and the entire plant can reach a height between 55-75 cm. The leaves are wide, 5-6 cm (average measured at the widest part of the mature leaf) and lanceolate with a soft waxy texture. The plant has a cylindrical shape.

The new variety is moderately drought tolerant, adapts to conditions of light and shade, and shows resistance to anthracnose (*Colletotrichum sansevieriae*) disease.

Plants of the new *Sansevieria* 'WHITE STAR' differ from plants of the parental cultivar, 'Marlowe' (U.S. Plant Pat. No. 34,061) in the characteristics described in Table 1.

TABLE 1

Comparison with Parental Varieties

| Characteristic | New Cultivar 'WHITE STAR' | Parent 'Marlowe' (U.S. Plant Pat. No. 34,061) |
|---|---|---|
| Plant Vigor | Less vigor (less leaves). | More vigor (more leaves). |

TABLE 1-continued

| Comparison with Parental Varieties | | |
|---|---|---|
| Characteristic | New Cultivar 'WHITE STAR' | Parent 'Marlowe' (U.S. Plant Pat. No. 34,061) |
| Color | Dark and light green with white colored irregular bands in the front and backside of the leaf blade. The light green and white stripes, cover more of the leaf blade. The under surface leaf, has a wider central vertical band that is white with variable light green striping, while the upper surface leaf has narrower central vertical band that is white with variable light green striping. | Variegated leaves (different green tones on the irregular bands). The colored stripes have a vertical display on both sides of the leaves. |
| Shape | Wide, curved and lanceolate leaves in a rosette. | Wide and lanceolate leaves in a rosette. |
| Texture of leaves | Smooth-textured leaves. | Smooth-textured leaves. |

Of the many commercial cultivars known to the present inventor, the most similar in comparison to the new *Sansevieria* 'WHITE STAR' is its parent, *Sansevieria* 'Marlowe' (U.S. Plant Pat. No. 34,061) in the characteristics described in Table 1.

BRIEF DESCRIPTION OF THE PHOTOGRAPHS

The accompanying photographs illustrate the overall appearance of the new *Sansevieria* cultivar 'WHITE STAR' showing the colors as true as is reasonably possible with colored reproductions of this type. Colors in the photographs may differ slightly from the color value cited in the detailed botanical description which accurately describe the color of 'WHITE STAR'.

FIG. 1—Shows a side view of a six-month old plant of *Sansevieria* 'WHITE STAR' in a 26 cm diameter pot.

Figure 2:
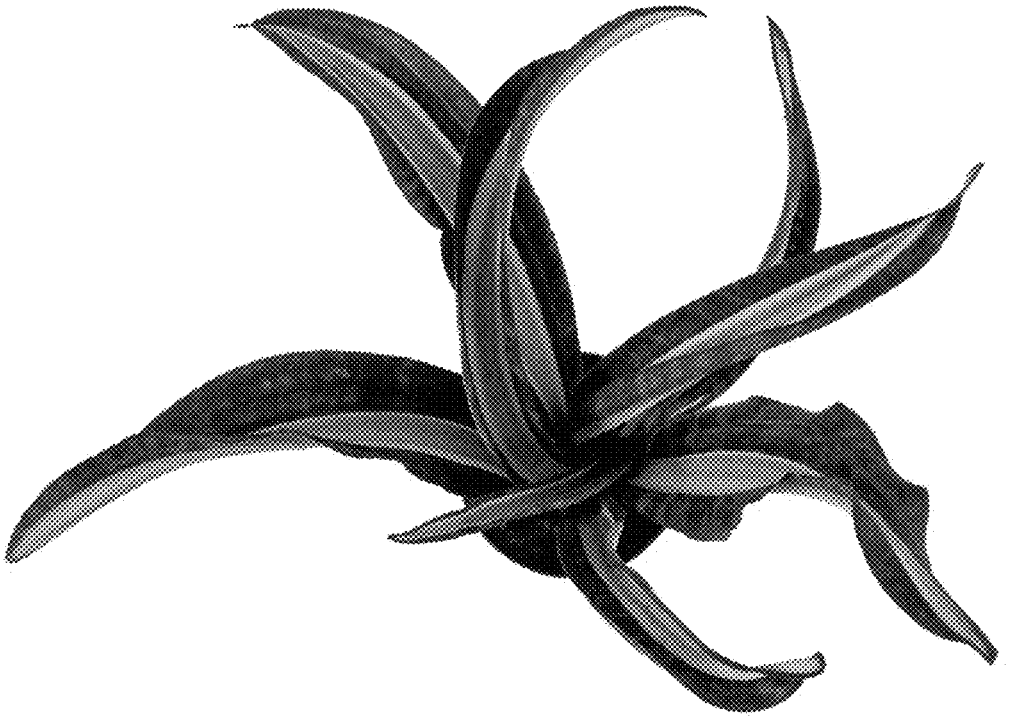

FIG. 2—Shows a pot down view of a typical six-month-old plant of *Sansevieria* 'WHITE STAR'.

Figure 3:
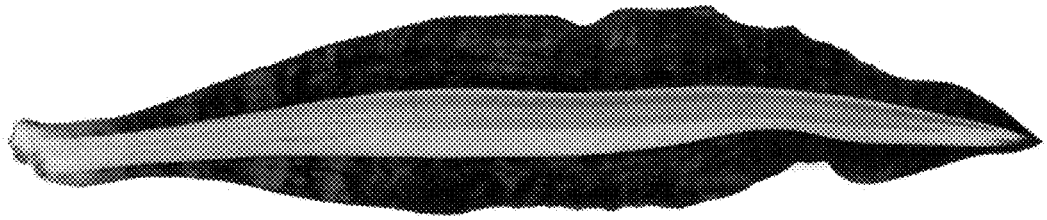
Figure 3:
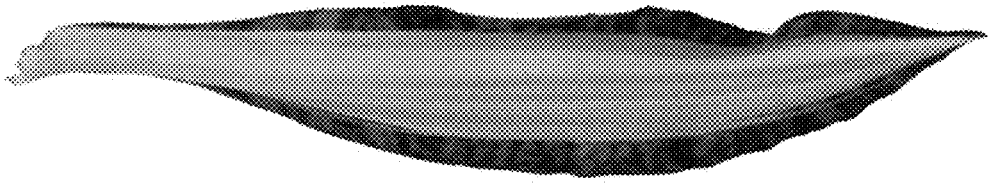

FIG. 3—Shows a close-up view of the typical leaves of *Sansevieria* 'WHITE STAR' from a six-month old plant (upper side—A, under side—B).

DETAILED BOTANICAL DESCRIPTION

The new *Sansevieria* 'WHITE STAR' has not been observed under all possible environmental conditions. The phenotype of the new cultivar may vary with variations in environment such as temperature, light intensity, and day length without any change in the genotype of the plant.

The photographs, together with the following observations, measurements and values describe the new *Sansevieria* cultivar 'WHITE STAR' as grown in open field conditions in Monterrey, San Carlos, Alajuela province, Costa Rica, which closely approximate those generally used in commercial practice. 'WHITE STAR' was grown in tropical lowlands in Costa Rica with day lengths of 12 to 13 hours and ambient temperature to 85 degrees. The level of relative humidity was 80%. No supplementary artificial light is necessary.

This crop does not require constant fertilization, to increase production per area about 200 kg ha-1 N, 150 kg ha-1 of P and 100 kg-ha K are required, the production is closely related with soil conditions in which they are grown.

Color references are made to The Royal Horticultural Society Colour Chart (R.H.S. 2015), except where general colors of ordinary significance are used. The photographs and descriptions were taken during the rainy season in Monterrey, San Carlos, Alajuela province, Costa Rica, with outdoor day temperatures of 24.5° C. during the day and 18° C. at night. The age of the plants described is 8 months.

Classification:

*Botanical.*—*Sansevieria aubrytiana.*

*Variety denomination.*—'WHITE STAR'.

Parentage: *Sansevieria aubrytiana* 'Marlowe' (U.S. Plant Pat. No. 34,061).

Optimal growth conditions:

*Light intensities.*—High adaptability to outdoor or indoor conditions.

*Temperature.*—Day: 24° C. to 32° C. Night: 18° C. to 23° C.

*Temperature tolerance.*—Tolerant to a low temperature of about 12° C. and tolerant to a high temperature of about 35° C.

*Fertilization.*—200, 150 and 100 kg $ha^{-1}$ of N, P and K.

*Growth regulators.*—Not necessary.

Propagation:

*Type.*—Vegetative, by rooted cuttings.

*Rooting habit and description.*—Rhizomes, with short roots.

*Time to initiate roots.*—About 12 to 22 days at 20-25° C.

*Time to produce a rooted cutting.*—About 15 to 22 days at 20-22° C.

Plant:

*General appearance and form:*

*Height.*—About 80 cm when grown in ground. About 60 cm when grown in a 26 cm size container.

*Spread.*—About 15 cm when grown in ground. About 12 cm when grown in 26 cm size container.

*Form.*—Monocot; leaf bases arranged in a rosette around growth point.

*Shape.*—Cylindrical.

*Growth rate and habit.*—About 2 cm per week; upright.

*Fragrance.*—None.

*Stem.*—Modified (Rhizome and foliage). Length: About 12 cm when grown in ground. About 8 cm when grown in 21 cm size container. Diameter: About 3.0 cm to 4.0 cm. Shape: Round. Texture: Rough. Color: RHS 4D. Strength: Strong and durable. Internode length: About 0.6 mm to 0.8 mm.

Foliage:

*Quantity.*—About 5-7 leaves.

*Arrangement and attachment.*—Single, alternate; leaf bases arranged in a rosette around growth point.

*Leaf length.*—About 30 cm.

*Leaf width.*—About 9 cm.

*Overall shape of leaf.*—Lanceolate.

*Apex shape.*—Acute, triangular.

*Base shape.*—Plane.

*Margin.*—Sharp, slightly sinuate.

*Texture*.—Upper Surface: Smooth and waxy texture. Under Surface: Smooth and waxy texture.

*Pubescence*.—Upper Surface: None. Lower Surface: None.

*Color of mature leaf*.—Upper Surface: RHS 141 A and RHS 130 D. Narrow Central Vertical Band: RHS 130 D and RHS 130 C. Narrow Central Vertical Band Margins: RHS NN155 C. Dark Leaf Margins: RHS 141 A and RHS 139 A. Wide Central Vertical Band: RHS 130 D. Lower Surface: RHS 141 A and RHS 130 D.

*Color of immature leaf*.—Upper Surface: RHS 141 A (along the margin) and RHS 130 D (Central vertical band). Narrow Central Vertical Band: RHS 130 D and RHS 130 C. Narrow Central Vertical Band Margins: RHS NN155 C. Dark Leaf Margins: RHS 141 A and RHS 139 A. Wide Central Vertical Band: RHS 130 D. Lower Surface: RHS 141 A (along the margin) and RHS 130 D (Central vertical band).

*Venation*.—Pattern: Longitudinal/parallel leaf shape. Color: None.

*Leaf fragrance*.—None.

Inflorescence description:

*Arrangement and type*.—Inflorescence.

*Orientation at opening*.—Upper orientation regarding the spile.

*Quantity*.—Per Plant with at least one open flower: About 60 at 2 weeks.

*Inflorescence size*.—Length: About 35 cm. Diameter: About 1.2 cm.

*Flower size*.—Length: About 6 cm. Diameter: About 0.5 cm. Depth: About 0.5 cm.

*Fragrance*.—None.

*Bud*.—

*Rate of opening*.—About 7 to 8 days, according to weather.

*Shape*.—Ovoid.

*Length*.—About 2 cm.

*Diameter*.—About 1 cm.

*Color*.—Apex: RHS 149 B. Base: RHS 142 B.

*Texture* (*both surfaces*).—Smooth.

Reproductive organs:

*Androecium*.—Stamen: Number: 6 per flower. Length: About 1.2 mm. Color: RHS 150 D. Anther: Length: About 4 mm. Width: About 1 mm. Color: RHS 150 D. Filament: Length: About 1.3 mm. Color: RHS 150 D. Pollen: Amount: Moderate. Color: RHS 150D.

*Gynoecium*.—Pistil: Number: One per flower. Length: About 1.5 mm. Stigma: Length: About 0.5 mm. Width: About 1 mm. Color: RHS 150 D. Style: Length: About 20 mm. Color: RHS 150 D. Ovary: Length: About 5 mm. Width: About 4 mm. Color: RHS 143 A.

Weather resistance: Moderately Drought Tolerant.

Disease/pest resistance: High resistance to anthracnose (*Colletotrichum sansevieriae*).

Disease/pest susceptibility: Not observed so far.

I claim:

1. A new and distinct *Sansevieria* plant named 'WHITE STAR', substantially as illustrated, and described herein.

* * * * *

A

B